US006789273B2

(12) United States Patent
Markovitz

(10) Patent No.: US 6,789,273 B2
(45) Date of Patent: Sep. 14, 2004

(54) PROTECTIVE EYEWEAR SYSTEMS AND METHODS

(76) Inventor: Aaron Markovitz, 888 Logan St. Number 11A, Denver, CO (US) 80203

( * ) Notice: Subject to any disclaimer, the term of this patent is extended or adjusted under 35 U.S.C. 154(b) by 0 days.

(21) Appl. No.: 10/063,821

(22) Filed: May 15, 2002

(65) Prior Publication Data

US 2003/0019018 A1 Jan. 30, 2003

Related U.S. Application Data

(60) Provisional application No. 60/291,305, filed on May 16, 2001, now abandoned.

(51) Int. Cl.[7] .................................................. A61F 9/02
(52) U.S. Cl. ............................................. 2/436; 2/452
(58) Field of Search ........................ 2/12, 13, 15, 426, 2/428, 431, 436, 441, 442, 443, 452; 24/3.3; 351/47, 57

(56) References Cited

U.S. PATENT DOCUMENTS 5,410,763 A * 5/1995 Bolle ............................. 2/436
5,657,106 A * 8/1997 Herald, Jr. et al. ........... 351/57
5,882,101 A * 3/1999 Chao ............................ 351/47
6,113,234 A * 9/2000 Huang ......................... 351/47
6,247,811 B1 * 6/2001 Rhoades et al. ............... 2/431
6,317,897 B1 * 11/2001 Chiang ......................... 2/428
6,405,384 B1 * 6/2002 Chiang ......................... 2/428
6,446,272 B1 * 9/2002 Lee .............................. 2/428
6,550,912 B2 * 4/2003 Vitaloni ....................... 351/47
6,550,913 B2 * 4/2003 Zelman ........................ 351/57

OTHER PUBLICATIONS

U.S. patent application Publication, US 2002/0157175, Dondero, John, 31 Oct. 2002.*

* cited by examiner

Primary Examiner—Gary L. Welch
(74) Attorney, Agent, or Firm—Webb Lewis + Meyers LLC; Glenn L. Webb

(57) ABSTRACT

Multifunctional protective eyewear that includes two or more lens assemblies that are quickly interchangeable to suit various environmental and situational conditions. The eyewear has particular applicability for tactical and ballistic use as well as motor sports, active sports and uses involving helmets. The strap system of a preferred embodiment can be quickly changed for either over the helmet use or under the helmet use.

19 Claims, 5 Drawing Sheets

| Thermal (sealed) | Single Lens | Under Helmet | Integrated Lens |
| --- | --- | --- | --- |
| Thermal (sealed) | Single Lens | Under Helmet | Interchangeable Lens |
| Thermal (sealed) | Single Lens | Over Helmet | Integrated Lens |
| Thermal (sealed) | Single Lens | Over Helmet | Interchangeable Lens |
| Thermal (sealed) | Double Lens | Under Helmet | Integrated Lens |
| Thermal (sealed) | Double Lens | Under Helmet | Interchangeable Lens |
| Thermal (sealed) | Double Lens | Over Helmet | Integrated Lens |
| Thermal (sealed) | Double Lens | Over Helmet | Interchangeable Lens |
| Ventilated | Single Lens | Under Helmet | Integrated Lens |
| Ventilated | Single Lens | Under Helmet | Interchangeable Lens |
| Ventilated | Single Lens | Over Helmet | Integrated Lens |
| Ventilated | Single Lens | Over Helmet | Interchangeable Lens |
| Ventilated | Double Lens | Under Helmet | Integrated Lens |
| Ventilated | Double Lens | Under Helmet | Interchangeable Lens |
| Ventilated | Double Lens | Over Helmet | Integrated Lens |
| Ventilated | Double Lens | Over Helmet | Interchangeable Lens |

*Figure 7*

PROTECTIVE EYEWEAR SYSTEMS AND METHODS

BACKGROUND OF INVENTION

The present invention provides multifunctional protective eyewear, particularly for ballistic and tactical use as well as other types of use. Protective eyewear is often necessary in many environments in order to protect and/or enhance the eyesight of individuals. These environments can include wind, dust, glare, weather, radiation, particles and many other types of conditions and environments. Often, an individual may need multiple lenses to accommodate differing and harsh environments. For example, it may be necessary to use a first lens for changing light conditions and a second lens for protection from debris. Also, many individuals require a first prescription lens and a second protective lens.

Another problem is with moisture and vapor buildup on the lens of goggles. This can impair the vision of the individual wearing the goggles. This often occurs from non-ventilated lens acquiring vapor from the individual and the environment.

These goggle and other eyewear systems can be expensive. Also, it may be cumbersome to transport different protective eyewear systems depending on the conditions to be encountered. Also, time may be critical in changing over protective eyewear systems.

Protective eyewear is often used with helmets for activities ranging from tactical use, by military, police, emergency workers, to sports such as motorcycles, sport shooting, skiing, snowboarding and many other uses. A common problem arises with the use of protective eyewear in a comfortable and effective manner with helmets. Sometimes the protective eyewear is worn with the strap beneath the helmet while other times the strap is worn over the helmet. If the strap is worn beneath the helmet, it may be bulky and compress uncomfortably against the sides of the wearer's head. If the strap is worn over the helmet, it may pull away from the wearer's face and break the sealing engagement between the eyewear and the wearer's face.

Another problem arises with the use of other eyewear, such as prescriptive eyewear. There are special goggles intended for use over prescription eyewear, but these goggles tend to be expensive and have an increased profile. Also, sometimes the wearer may choose not to wear the prescription eyewear.

A serious drawback with existing protective eyewear is that such eyewear is intended for a single type of use. At most, such eyewear may allow interchangeability of lens for different light conditions. There presently is no protective eyewear that is truly suitable for use in many different environments. This can be a detriment in critical uses and at the very least can be an annoyance. For example, there are situations that require a sealed engagement for eye protection, whereas other times, an unsealed engagement may be preferable for comfort and ventilation. Also, there are times where the strap of the protective eyewear may be worn beneath a helmet, whereas other times, the strap may be worn over the helmet. There are also times when different lenses may need to be quickly changed. Additionally, there may be times when a single lens is sufficient while other times may require an additional lens for protection or other uses.

Thus, there presently is a need for a multi-functional protective eyewear system that enables users to easily and quickly change lens to accommodate the existing conditions.

SUMMARY OF INVENTION

The present invention provides a multifunctional protective eyewear system. In a preferred embodiment, the protective eyewear can be easily and quickly changed to various configurations to enable use in a multitude of uses and environments. This enables the wearer to be effective regardless of the encountered environment and/or situation. The protective eyewear is suitable for use in tactical situations, ballistic situations, around hazardous materials, sports, motorcycles, or any other situation requiring protective eyewear.

In one preferred embodiment, the protective eyewear includes one or more lens assemblies that are quickly interchangeable. The lens assemblies engage in detents in the side clips of the lens frame. This enables the lens assemblies to be quickly removed and reinserted. Thus, the lens assemblies can be interchanged as required. Different lens having different tints, protective layers or other characteristics can be used as desired.

In a preferred embodiment, two lens assemblies can be used by layering over one another. This allows a first lens assembly having particular characteristics such as tinting and a second lens assembly for protective against shrapnel or other ballistic environments, or in harsh environments. The outer lens assembly can be removed if not needed.

Another preferred embodiment allows each of the lens assemblies to be moved between a ventilated position and a thermal position. This is important in many environments where fogging, moisture condensation or other considerations may occur. This embodiment may also include a second lens assembly that is also movable between two or more positions.

The present invention also includes a preferred embodiment that uses the clips on the eyewear retaining strap to lock the lens assemblies in place. The clips engage detents or notches on the side tabs of the lens assemblies to lock the lens assemblies in position. The clips are easily disengaged to allow for quick reposition or removal of the lens assemblies.

The present invention also provides a unique locking system for the lens assemblies that is adjustable to compensate for over the helmet or under the helmet usage of the protective eyewear. This unique locking system enables quick change of the strap position to ensure comfort and protection of the wearer of the proactive eyewear.

These features and others of the present invention are provided individually as well in different combinations of one another. For example, in one preferred embodiment, the protective eyewear includes side tabs on each of the lens assemblies. The side tabs include one or more inner notches and outer detents. The frame of the protective eyewear includes side clips having notches and detents facing outward. The side tabs of the first lens assembly are inserted into the side clips until the inner notches engage in one of the detents of each of the side clips. The use of a plurality of notches or detents enable securing the first lens assembly in one or more positions. The side tabs of the second lens assembly is then inserted in the side clips over the side tabs of the first lens assembly. The inner notches of the side tabs of the second lens assembly engage the detents on the side tabs of the first lens assembly.

The securing clips of the strap include an offset aperture for engagement of the strap. Resilient tabs on the securing clips are then inserted in the side clips of the lens frame. These tabs exert pressure against the side tabs of the lens assemblies to lock the lens assemblies in place on the lens frame.

The offset strap aperture enables the protective eyewear to be worn under a helmet or over a helmet. Inserting the resilient tabs of the securing clips in the front of the lens frame causes the strap to extend outwardly from the lens frame so the strap goes around the exterior of the helmet. Inserting the resilient tabs of the securing clips of the rear of the lens frame causes the strap to extend inwardly from the lens frame so that it is away from the interior of the helmet for under the helmet usage.

The ease of removal and remounting of the lens assemblies as well as the ability to change the position of the strap mounting provides a multitude of the differing combinations for various environment and situational usages. These and other features will be evident from the ensuring detailed description of preferred embodiments and from the drawings.

BRIEF DESCRIPTION OF DRAWINGS

FIG. 7 is a table listing the various configurations of the goggles of the preferred embodiment of the present invention,

DETAILED DESCRIPTION

The present invention provides a multi-functional protective eyewear that is suitable for use in tactical, military, ballistic, sport and other uses. The protective eyewear of the present invention includes a low-profile, high-quality and quickly interchangeable system that is usable in many different environments, including differing light conditions, weather conditions, as well as protective environments ranging from wind, dust, shrapnel, glare, low light, etc., and in differing uses including with or without helmets, and over or under helmets. Also, the protective eyewear may be used in thermal environments to prevent fogging or to sealed from the environment. These and other features may be included in preferred embodiments of the present invention either in combination with one another or taken alone. Preferred embodiments are discussed below and are intended for explanatory purposes only and are not meant to limit the scope of the present invention.

A preferred embodiment of the present invention is illustrated in FIGS. 1–7.

Figure 1:
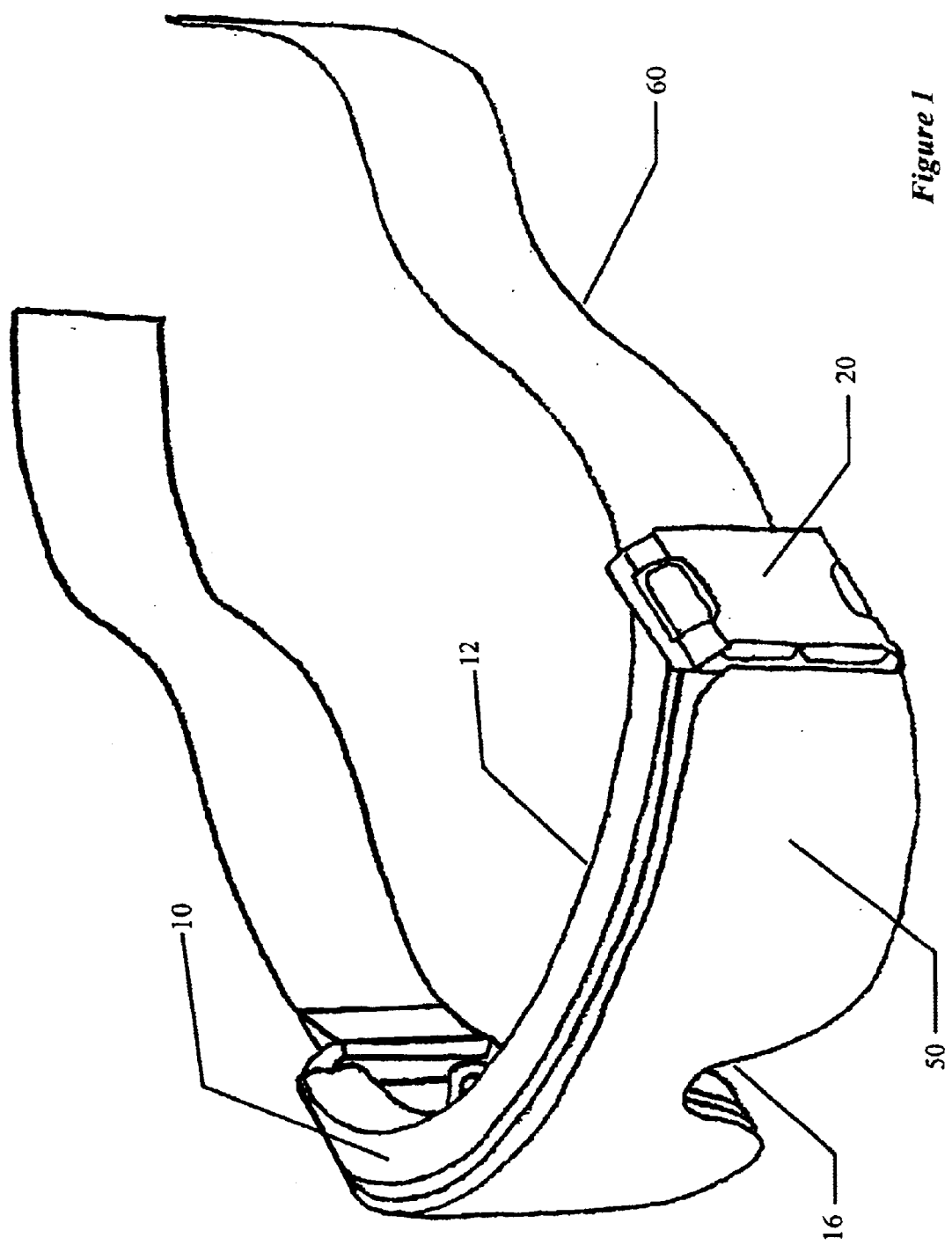
FIG. 1 is a perspective view of a preferred embodiment of the present invention.
Figure 2:
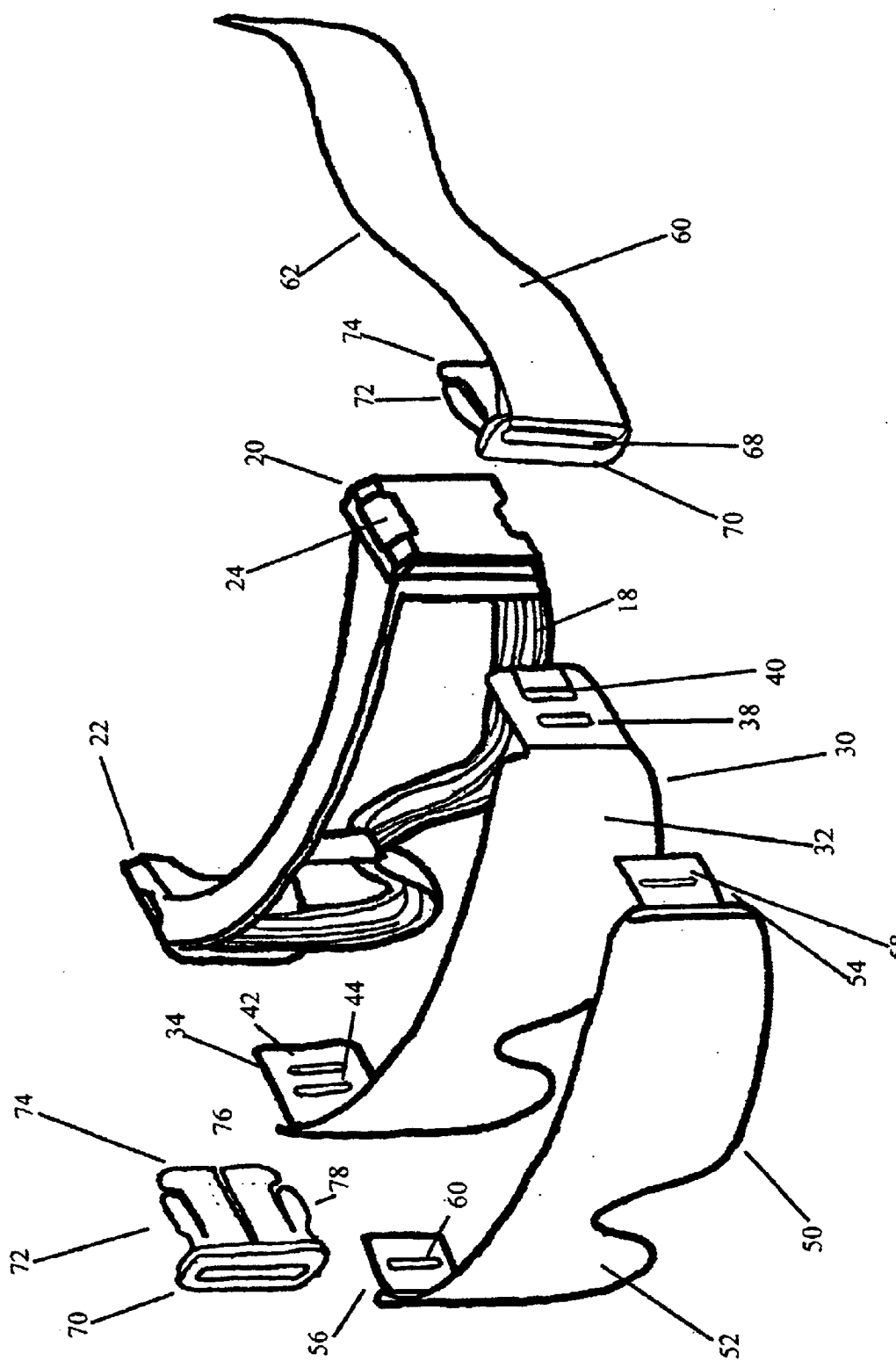
FIG. 2 is an exploded view of the embodiment of FIG. 1.

As shown in FIGS. 1 and 2, the protective eyewear of this preferred embodiment includes a frame 10, a first lens assembly 30, a second lens assembly 50 and a strap 60. The frame 10 has an inner portion 12 contoured to fit snugly about a user's face. In one preferred embodiment, the inner portion includes a flexible gasket (not shown) to ensure a sealed engagement with the face of a user. A nose portion 14 is shaped to comfortably fit over a user's nose, The outer portion 16 of the frame 10 includes a recessed portion 18 for receiving the first lens assembly 30.

The frame 10 also includes side clips 20, 22. These side clips, shown in detail in FIG. 6, include side notches 24, 26 (respectively on each clip) and inner detent 28 (there can also be addition inner detents as well).

The first lens assembly 30 includes a lens portion 32 and side tabs 34, 36. Each of the side tabs 34, 36 include outer detents 38, 40 and inner notches 42, 44, respectively. The lens portion 32 can be clear for protection against particles, wind and other airborne contaminates, colored for use in different environments or any other type of protective lens. The side tabs 34, 36 are sized to fit within the side clips 20, 22 of the frame 10. The outer edges of the lens assembly fit snugly within the recessed portion 18 of the frame. The lens assembly 30 is secured to the frame assembly by inserting the tabs 34, 36 into the clips 20, 22 of the frame assembly until at least one of the notches 42, 44 of the side tabs engage on detent 28 of the side clips 20, 22.

The use of two notches 42, 44 enable the first assembly to be engaged in one of two positions relative to the frame 10. The first position with notch 42 engaging the detent 28 provides the lens assembly spaced from the frame in a ventilated position. The second position with notch 44 engaging detent 28 secures the lens against the frame for thermal protection as well as other types of protection.

The second lens assembly 50 also includes a lens portion 52 and side tabs 54, 56. Each of the side tabs includes at least one detent 58 and inner notch 60. The lens portion 52 can be tinted to a suitable color in accordance with the available light or other environmental concerns. The second lens assembly 50 is secured to the frame 10 over the first lens assembly 30. The side tabs 54, 56 are inserted into the side clips 20, 22 over the side tabs 34, 36 of the first lens assembly. The inner notch 60 engages one of the outer detents 38, 40 of the side tabs 34, 36. This allows the second lens to be secured in one of two or more positions depending on how many detents and/or notches are provided. For example, the lens 50 can be locked in a first position with inner notches 60 engaging over detents 38 of tabs 34, 36. This provides a ventilated position. The lens 50 may also be pushed inward so that notches 60 engage detents 40 on tabs 34, 36. This provides a sealed position to minimize fogging and/or for thermal protection.

The first lens assembly 30 and second lens assembly 50 are locked to the frame assembly by the locking clips 64, 66 of the strap 60. Strap 60 includes a strap portion 62 and locking clips 64, 66. The locking clips 64, 66 each include an aperture 68 formed in side member 70 through which the strap portion 62 is inserted. Resilient tab members 72 and 78 are formed substantially parallel to clip members 74, 76 extending perpendicularly from the side member 70. The locking clips 64, 66 are inserted into side clips 20, 22 of the frame assembly 10 over either the slide tabs 34, 36 of the first lens assembly 30 if only one lens is used or over the side tabs 54, 56 of the second lens assembly 50 if both lens are used. The resilient tab members 72, 78 are engaged in the notches 24, 26 of the side clips 20, 22 to lock the locking clips into engagement with the frame assembly.

Figure 3:
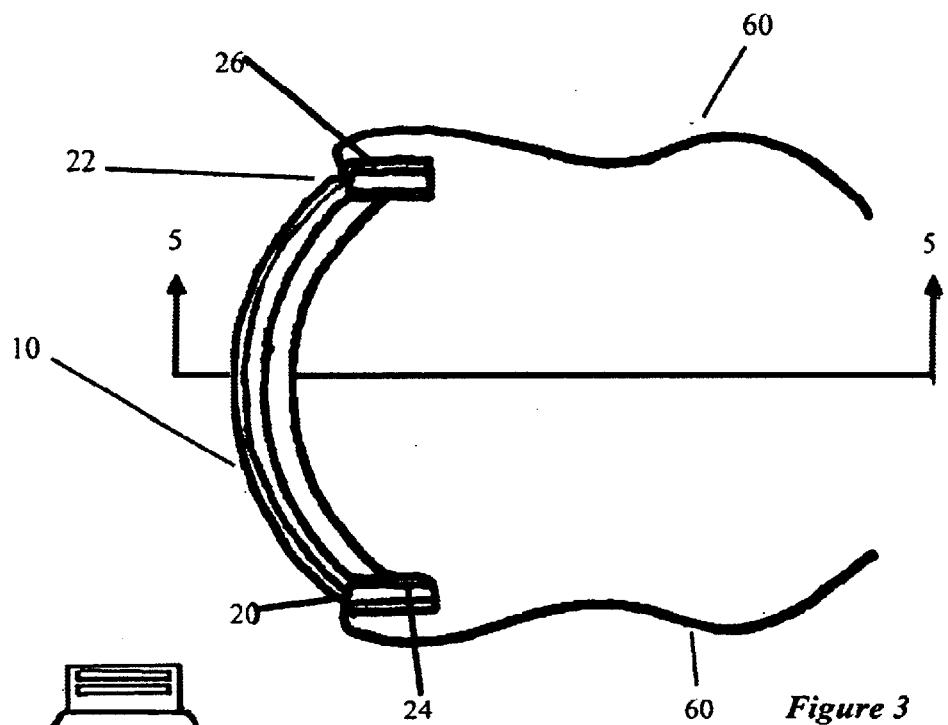
FIG. 3 is a top view of the embodiment of FIG. 1.
Figure 4:
FIG. 4 is a front view of the embodiment of FIG. 1.
Figure 5:
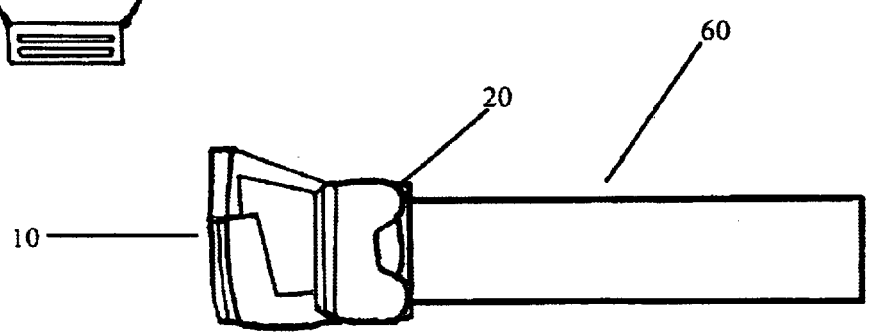
FIG. 5 is a cross-sectional view of the embodiment of FIG. 1.
Figure 6:
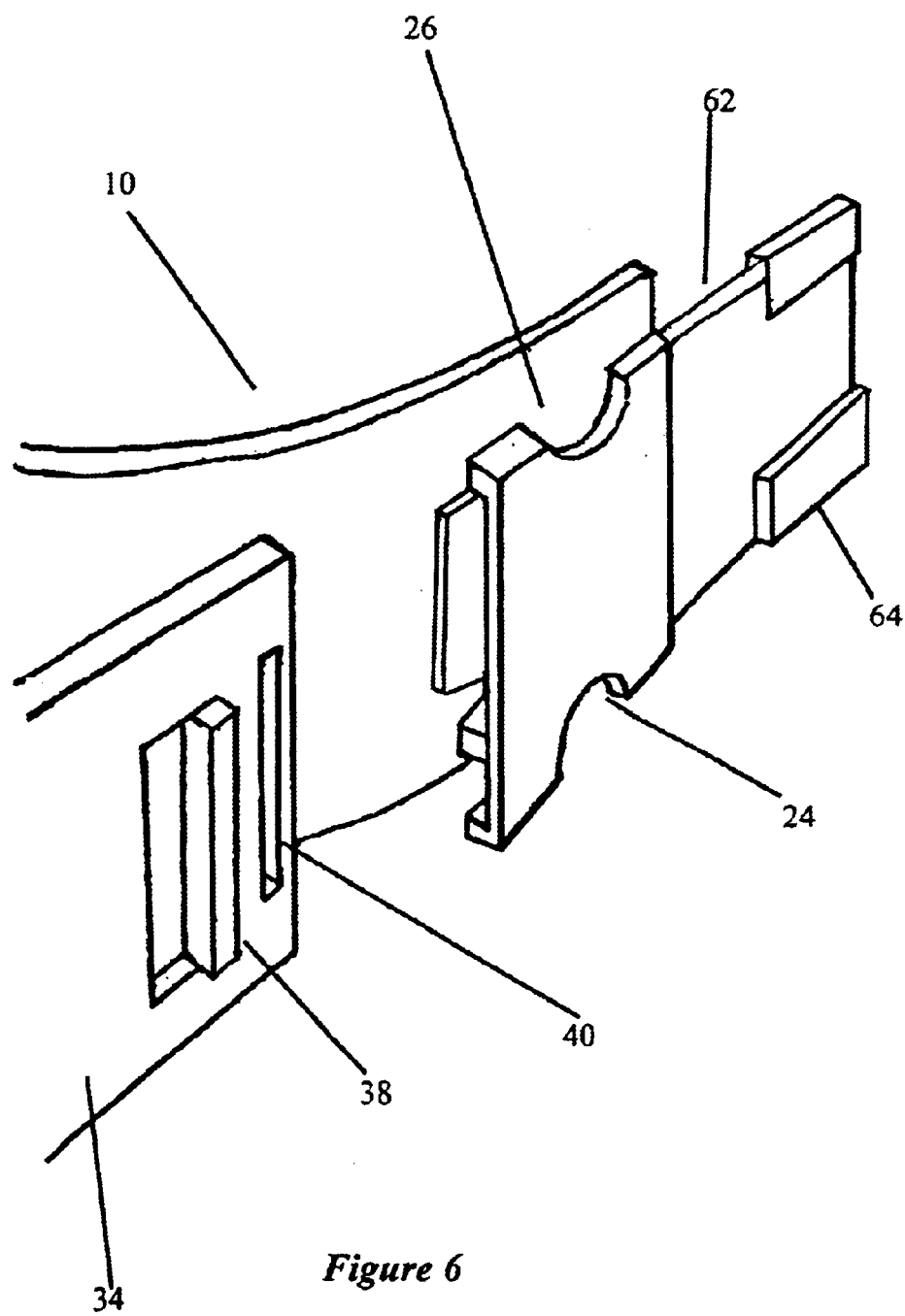
FIG. 6 is a view of the locking clip.

The locking clips can engage the side clips of the frame assembly 10 from the rear as shown in FIG. 1 or if the strap is required to go over a helmet or other protective head gear, the ends of the strap can be reversed and inserted from the front of the frame assembly as shown in FIG. 2. This provides a more versatile protective eyewear assembly. This is critical in many applications. For example, in many tactical situations the strap must go over the helmet. The ability of the strap to fasten to the front of the lens assembly and offset on the outer side of the frame 10 as shown in FIGS. 2 and 3 minimizes pulling from the strap over the helmet. This assists in the sealing of the protective eyewear against the face of the wearer. Alternatively, if the strap is to be worn under the helmet, the strap is fastened to the inner surface of the locking clips as shown in FIG. 1. The offset of the strap is to the interior of the frame of the protective eyewear and minimizes crushing of the strap against the wearer from the helmet.

The lens assemblies can be removed or adjusted to the ventilated or non-ventilated position by simply pressing down on the resilient tab members 72, 78 through the notches 24, 26 and removing the locking clips from the side clips. This allows the lens to be changed or adjusted very quickly and without the need for special tools.

This preferred embodiment provides a multi-functional protective eyewear that can be quickly and easily adjusted to a number of various configurations. For example, the protective eyewear could be adjusted at a minimum to the following configurations as set forth in FIG. 7.

Many other configurations are available as well, for instance, by have a plurality of interchangeable lens for use in differing light or environmental conditions. Different tints are available for different light conditions, as well as different compositions for use with different wavelengths, such as laser, infrared, night vision, radiation and other environments. Also, different lenses may be desired for other conditions and functions, such as ballistic lens for use around shrapnel or high dust storms, thermal lenses for use in extreme conditions, anti-fog lens, and other lens for other conditions.

In another preferred embodiment, a separate clip (not shown) having a side tab similar to the side tabs of the lens assemblies can be utilized. The separate clip can have tools, such as nighttime vision eyepieces, telescopic sights or other useful fixtures mounted to it. This enables the goggles of the present invention utilize other lens and/or tools easily interchangeable as needed. The separate side clip can also be hinged so it can be swiveled out of the way when not in use. This side clip, in another preferred embodiment, is integrated with the strap locking clip to provide additional support.

In another preferred embodiment, a tear-away lens portion (not shown) is used with either the first lens assembly, second lens assembly or both. The tear-away lens portion enables the outer surface of the lens portion to be quickly removed and an underneath lens portion exposed for continued use. This is particularly useful in an abrasive and/or quick-fire environment.

In another preferred embodiment (not shown) a prescription lens is used as the first or second lens assembly. This enables either a single person to use multiple goggle systems, a single goggle to be used with multiple users, or a user to use prescription lens only as needed.

These and other features are provided by the present invention. It is to be expressly understood that the present invention is not meant to be limited to the descriptive embodiments that are provided for explanatory purposes only.

What is claimed is:

1. A protective eyewear system, the protective eyewear system comprising:

a frame having side clips;

a first lens assembly having side tabs engageable in said side clips;

two or more notches spaced from one another on said side tabs for engagement with said side clips to provide a first engagement position of said first assembly away from said frame and a second engagement position of said first lens assembly against said frame; and a strap having locking clips engageable in said side clips against said outer side tabs.

2. The protective eyewear system of claim 1 wherein said each of side tabs includes:

at least one notch; and said side clips includes at least one detent for engaging said at least one lens assembly by aligning said at least one notch of said side tabs.

3. The protective eyewear system of claim 1 wherein said protective eyewear system includes:

said side tabs of said first lens assembly having at least one notch on the inner surface of said side tabs and at least one detent on the outer surface of said side tabs;

at least one detent on said side clips for engagement with said at least one notch on said side tabs of said first lens assembly;

a second lens assembly having side tabs, and at least one notch on the inner surface of said side tabs of said second lens assembly for engagement with said at least one detent on the outer surface of said side tabs of said first lens assembly as said first lens assembly and said second lens assembly are inserted in said side clips.

4. The protective eyewear system of claim 1 wherein said protective eyewear system includes:

said side tabs of said first lens assembly having at least two notches on the inner surface of said side tabs and at least one detent on the outer surface of said side tabs;

at least one detent on said side clips for engagement with one of said at least two notches on said side tabs of said first lens assembly to allow said first lens assembly to be engaged in at least two positions relative to said frame;

a second lens assembly having side tabs, and at least two notches on the inner surface of said side tabs of said second lens assembly for engagement with said at least one detent on the outer surface of said side tabs of said first lens assembly as said first lens assembly and said second lens assembly are inserted in said side clips to allow said second lens assembly to be engaged in at least two positions relative to said frame.

5. The protective eyewear system of claim 1 wherein said locking clips of said strap include:

a locking member for engagement with said side clips;

an aperture offset from said locking member for retaining said strap, in a position which allows said strap to engage with said outer side clips away from said frame.

6. The protective eyewear system of claim 5 wherein said locking clips include:

resilient tabs that are insertable in said side clips in a first position in the front of said frame so that said offset aperture extends outwardly from said frame and a second position in the rear of said frame so that said offset aperture extends inwardly from said frame.

7. The protective eyewear system of claim 1 wherein said locking clips include:

resilient tabs that are inserted in said side clips of said frame to lock said side tabs of said first lens assembly relative to said frame.

8. A protective eyewear system, the protective eyewear system comprising:

a frame having side clips;

a first lens assembly having side tabs engageable in at least one position of said side clips;

a strap having locking clips engageable in said outer side clips against said outer side tabs; and a second lens assembly having side tabs engageable over said first lens assembly side tabs and in said side clips.

9. A protective eyewear system, the protective eyewear system comprising:

a frame having side clips;

a lens assembly engaged on said frame;

a strap for securing said frame to a wearer;

locking clips selectively engageable on said frame in a first position on the front area of said frame and a second position on the rear of said frame;

locking members on each of said locking clips to engage said frame in either said first position or said second position; and an aperture on each of said locking clips offset from said locking members for receiving said strap so that said strap extends away from said frame when said locking clips are engaged in said first position and said strap extends inward of said frame when said locking clips are engaged in said second position.

10. The protective eyewear system of claim 9 wherein said lens assembly includes side tabs having at least one notch on the inner surface of each said side tabs; and said side clips of said frame include at least one detent for engaging said at least one lens assembly by aligning said at least one notch of said side tabs as said tabs are inserted in said side clips.

11. The protective eyewear system of claim 10 wherein said side tabs include:

two or more notches for engagement with at least one detent in said side clips to provide a first engagement position, away from said frame and a second engagement position against said frame.

12. The protective eyewear system of claim 10 wherein said protective eyewear system includes:

said side tabs of said lens assembly having at least one notch on the inner surface of said side tabs and at least one detent on the outer surface of said side tabs;

at least one detent on said side clips for engagement with said at least one notch on said side tabs of said lens assembly;

a second lens assembly having side tabs, and at least one notch on the inner surface of said side tabs of said second lens assembly for engagement with said at least one detent on the outer surface of said side tabs of said first lens assembly as said first lens assembly and said second lens assembly are inserted in said side clips.

13. The protective eyewear system of claim 10 wherein said protective eyewear system includes:

said side tabs of said lens assembly having at least two notches on the inner surface of said side tabs and at least one detent on the outer surface of said side tabs;

at least one detent on said side clips for engagement with one of said at least two notches on said side tabs of said lens assembly to allow said lens assembly to be engaged in at least two positions relative to said frame;

a second lens assembly having side tabs, and at least two notches on the inner surface of said side tabs of said second lens assembly for engagement with said at least one detent on the outer surface of said side tabs of said lens assembly as said lens assembly and said second lens assembly are inserted in said side clips to allow said second lens assembly to be engaged in at least two positions relative to said frame.

14. The protective eyewear system of claim 10 wherein said locking clips include:

resilient tabs that are inserted in said side clips of said frame to lock said side tabs of said first lens assembly relative to said frame.

15. A protective eyewear system, the protective eyewear system comprising:

a frame having side clips;

a lens assembly engaged on said frame; and a strap for securing said frame to a wearer;

locking clips having locking members selectively engageable in said side clips in a first position on the front facing area of said side clips and a second position on the rear facing area of said side clips; and an aperture on each of said locking clips offset from said locking members for receiving said strap so that said strap extends away from said frame when said locking clips are engaged in said first position and said strap extends inward of said frame when said locking clips are engaged in said second position;

said lens assembly includes side tabs having at least one notch on the inner surface of each said side tabs;

said side clips of said frame include at least one detent for engaging said at least one lens assembly by aligning at least one notch of said side tabs as said tabs are inserted in said side clips; and a second lens assembly having side tabs engageable over said first lens assembly side tabs and in said side clips.

16. The protective eyewear system of claim 15 wherein said locking clips include:

resilient tabs that are insertable in said side clips of said frame to lock said side tabs of said first lens assembly and said second lens assembly relative to said frame.

17. A method for using a multi-function protective eyewear having a frame with side clips, at least one lens assembly securable to said frame, a strap for retaining said eyewear to a user, locking clips having a locking member for engaging said side clips of said frame and an aperture offset from said locking members on said locking clips for receiving said strap, said method comprising:

inserting said locking clips in the front of said side clips so that said aperture extends away from said frame for use of the protective eyewear with said strap over a helmet; and inserting said locking clips in the rear of said side clips so that said aperture extends inwardly at said frame for use of the protective eyewear with said strap under a helmet.

18. The method of claim 17 wherein said method further includes:

side tabs on said at least one lens assembly that engage in said side clips in one or more positions.

19. The method of claim 18 wherein said method further includes:

a second lens assembly with side tabs that engage in said side clips in one or more positions.

* * * * *